(12) United States Patent
Stern et al.

(10) Patent No.: US 7,354,904 B2
(45) Date of Patent: Apr. 8, 2008

(54) BACTERIOCIN INDUCER PEPTIDES

(75) Inventors: Norman J. Stern, Athens, GA (US);
Edward A. Svetoch, Serpukhov (RU);
Boris V. Eruslanov, Serpukhov (RU);
Vladimir V. Perelygin, Serpukhov (RU); Vladimir P. Levchuk, Serpukhov (RU)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/297,841

(22) Filed: Dec. 8, 2005

(65) Prior Publication Data

US 2007/0135339 A1 Jun. 14, 2007

(51) Int. Cl.
*A61K 38/00* (2006.01)
(52) U.S. Cl. .............................. 514/17; 514/12; 514/13
(58) Field of Classification Search .................... 514/12
See application file for complete search history.

(56) References Cited

U.S. PATENT DOCUMENTS 6,790,951 B1 9/2004 Eijsink et al.

OTHER PUBLICATIONS

Altermann, E., Russell W.M., Azcarate-Peril M.A., Barrangou R., Buck B.L., McAuliffe O., Souther N., Dobson A., Duong T., Callanan M., Lick S., Hamrick A., Cano R., and Klaenhammer T.R. "Complete genome sequence of the probiotic lactic acid bacterium Lactobacillus acidophilus NCFM." Proceedings of the National Academy of Science USA; 102:3906-3912, 2005.*

Risoen, Per Arne et al., "Functional analysis of promoters involved in quorum sensing-based regulation of bacteriocin production in Lactobacillus," *Molecular Microbiology*, 2000, vol. 37 (3), pp. 619-628.

Lory, Stephen, "Secretion of proteins and assembly of bacterial surface organelles: shared pathways of extracellular protein targeting," *Microbiology*, 1998, vol. 1, pp. 27-35.

Cotter, Paul et al., "Bacteriocins: Developing Innate Immunity for Food," *Nature Reviews/Microbiology*, Oct. 2005, vol. 3, pp. 777-788.

De Kievit, Teresa R. et al., "Bacterial Quorum Sensing in Pathogenic Relationships," *Infection and Immunity*, Sep. 2000, vol. 68, No. 9, pp. 4839-4849.

Herranz, Carmen et al., "Sec-Mediated Secretion of Bacteriocin Enterocin P by Latococcus Lactis," website; www.aem.asm.org, pp. 1.

(Continued)

*Primary Examiner*—Jon Weber
*Assistant Examiner*—Hugh P. Young
(74) *Attorney, Agent, or Firm*—John D. Fado; Gail E. Poulos

(57) ABSTRACT

Novel peptides produced by bacteriocin-producing bacteria stimulate the production of bacteriocins in vitro. The producer bacteria are cultured in the presence of a novel inducer bacteria and a peptide having a carboxy terminal sequence of VKGLT in order to achieve an increase in bacteriocin production.

4 Claims, 3 Drawing Sheets
(3 of 3 Drawing Sheet(s) Filed in Color)

A 1  2  3

B 1  2  3

OTHER PUBLICATIONS

Svetoch, Edward et al., "Isolation of *Bacillus circulans* and *Paenibacillus* polymyxa Strains Inhibitory to Campylobaxter *jejuni* and Characterization of Associated Bacteriocins," *Journal of Food Protection*, 2005, vol. 68, No. 1, pp. 11-17.

Chen, H et al., "Bacteriocins and their Food Application," *Comprehensive Reviews in Food Science and Food Safety*, 2003, vol. 2, pp. 82-100.

Diep, Dzung B. et al., "Inducible bacteriocin production in *Lactobacillus* is regulated by differential expression of the *pln* operons and by two antagonizing response regulators, the activity of which is enhanced upon phosphorylation," *Molecular Microbiology*, 2003, vol. 47 (2), pp. 483-494.

Diep, Dzung B. et al., "Evidence for dual functionality of the operon *plnABCD* in the regulation of bacteriocin production in Lactobacillus plantarum," *Molecular Microbiology*, 2001, vol. 41(3), pp. 663-644.

Van Belkum, Marco J. et al., "Nonlantibiotic antibacterial peptides from lactic acid bacteria," *Nat. Prod. Rep.*, 2000, vol. 17, pp. 323-335.

Kleerebezem, Michiel et al., "Quorum sensing by peptide pheromones and two-component signal-transduction systems in Gram-positive bacteria," *Molecular Microbiology*, 1997, vol. 24 (5), pp. 895-904.

Cintas, Luis M. et al., "Enterocins L50A and L50B, Two Novel Bacteriocins from *Enterococcus faecium* L50, Are related to Staphylococcal Hemolysins," *Journal of Bacteriology*, Apr. 1998, vol. 180, No. 8, pp. 1988-1994.

\* cited by examiner

A  B 1  2  3        1  2  3

A 　　B

A                          B

US 7,354,904 B2

BACTERIOCIN INDUCER PEPTIDES

BACKGROUND OF THE INVENTION

1. Field of the Invention

This invention relates to novel peptides that stimulate the production of bacteriocins by producer bacteria in the presence of inducer bacteria and to methods for using the peptides for bacteriocin production.

2. Description of the Related Art

Normal intestinal bacteria are critical to the health of any host animal. The host derives benefit through the digestive metabolic processes mediated by the native bacterial biota. From the perspective of the intestinal bacteria, competition and consequent evolution provide nutrients and living space and increase reproductive potential, enabling certain strains and species to gain survival advantage. During bacterial evolution, bacteriocin production has occurred. Bacteriocins are antagonistic to other organisms within a given competitive niche and thus provide an ecological advantage. These bacteriocins are typically low-molecular-weight polypeptides and are classified based on differences in molecular weight (Klaenhammer, FEMS Microbiol. Rev., Volume 12-39-85, 1993). These compounds can be digested easily into their component amino acids by host protease enzymes. Bacteriocins may represent a significant component of the benefits derived from competitive exclusion (Nurmi and Rantala, Nature, London, Volume 241, 210-211, 1973).

Nurmi and Rantala (1973, supra) originally described the advantages of competitive exclusion in controlling *Salmonella* colonization among newly hatched chicks by using an undefined bacterial flora derived from the feces of healthy adult birds. This approach is an attractive alternative to current husbandry practices involving synthetic antibiotics. A mucosal derived competitive exclusion flora was described (Stern et al., U.S. Pat. No. 5,451,400, issued September 1995) as an anaerobic culture derived from the scrapings of the intestinal mucosal linings in healthy adult hens. This undefined flora provided excellent protection against *Salmonella* colonization in chickens but provided only inconsistent control of *Campylobacter* colonization (Stern, Poult. Sci, Volume 73, 402-407, 1994). Competitive exclusion occurs within the intestinal tract of wild birds and contributes to healthy gut ecology.

Microorganisms produce a variety of compounds which demonstrate anti-bacterial properties. One group of these compounds, the bacteriocins, consists of bactericidal proteins with a mechanism of action similar to ionophore antibiotics. Bacteriocins are often active against species which are closely related to the producer of the bacteriocin. Their widespread occurrence in bacterial species isolated from complex microbial communities such as the intestinal tract, the oral, or other epithelial surfaces, suggests that bacteriocins may have a regulatory role in terms of population dynamics within bacterial ecosystems. Bacteriocins are defined as compounds produced by bacteria that have a biologically active protein moiety and bactericidal action (Tagg et al., Bacteriological Reviews, Volume 40, 722-256, 1976). Other characteristics may include: (1) narrow inhibitory spectrum of activity centered about closely related species; (2) attachment to specific cell receptors; and (3) plasmid-borne genetic determinants of bacteriocin production and of host cell bacteriocin immunity. Incompletely defined antagonistic substances have been termed "bacteriocin-like substances". Some bacteriocins effective against Gram-positive bacteria, in contrast to Gram-negative bacteria, have wider spectrum of activity. It has been suggested that the term bacteriocin, when used to describe inhibitory agents produced by Gram-positive bacteria, should meet minimum criteria (1) being a peptide, and (2) possessing bactericidal activity (Tagg et al., supra).

In order to make commercial use of bacteriocins economically feasible, optimization of yield during production is necessary (Chen and Hoover, Comprehensive Reviews in Food Science and Food Safety, Volume 2, 82-100, 2003). Chen and Hoover state that for nisin production, it was found that in growth media, the key factors were maintenance of optimal pH and supplementation of the medium with specific nutrients for each strain or strains producing the bacteriocin.

Knutsen et al. (Journal of Bacteriology, Volume 186 (10), 3078-3085, 2004) disclose a bacteriocin inducing peptide (BIP) of 27 amino acids which induces bacteriocin production in *Streptococcus pneumoniae*. Diep et al. (Molecular Biology, Volume 47 (2), 483-494, 2003) discloses that a number of Gram-positive bacteria have been reported to apply a so-called peptide pheromone-based signal-transducing pathway to regulate the production of antimicrobial peptides, known as bacteriocins, from numerous lactic acid bacteria. They also disclose a peptide pheromone, PlnA, which induces bactericiocin production. Van Belkum and Stiles (Nat. Prod. Rep., Volume 17, 323-335, 2000) disclose that some bacteriocins require products of regulatory genes for their production. They state that these genes encode a secreted induction peptide and proteins that are homologous to histidine kinases and response regulators. The reference further discloses that some class II bacteriocins are induced by an induction peptide while others such as carnobacteriocin B2 and sakacin P are induced by an induction peptide or autoinduced by the synthesized bacteriocin.

While various peptides have been found which induce the production of bacteriocins in bacteria, there remains a need in the art for commercial production of bacteriocins using peptides which increase the yield of bacteriocin production in vitro. The present invention provides peptides which are different from prior art peptides and provides a method for producing large quantities of bacteriocins for commercial use.

SUMMARY OF THE INVENTION

It is therefore an object of the present invention to provide peptides which stimulate the production of bacteriocins in vitro.

A further object of the present invention is to provide peptides which stimulate the production of bacteriocins in vitro and have a carboxy terminal sequence of VKGLT (SEQ ID NO 1).

Another object of the present invention is to provide a peptide having the amino acid sequence: MVTKSLV-LAWVVALLACGMVKGLT (SEQ ID NO 3).

A further object of the present invention is to provide a peptide having the amino acid Sequence TNVTKSWWV-LAGCNQVVASNCNCGNVKGLT (SEQ ID NO 5).

A still further object of the present invention is to provide a peptide having the amino acid sequence of WNKYKT-NWVLSVCNTGCACAAVKGLT (SEQ ID NO 7).

Another object of the present invention is to provide a method for increasing the production of bacteriocins in vitro wherein a peptide having a carboxy terminal sequence of VKGLT (SEQ ID NO 1) is added to a culture of bacteriocin-producing cells.

A still further object of the present invention is to provide a method for increasing the production of bacteriocin OR-7 in vitro wherein a peptide having SEQ ID NO 3 is added to a culture of *Lactobacillus salivarius* PVD-32 (NRRL B-30514) cells.

Another object of the present invention is to provide a method for increasing the production of bacteriocin 50-52 in vitro wherein a peptide having SEQ ID NO 5 is added to a culture of *Enterococcus faecium* LWP 50-52 cells (NRRL B-30746).

A still further object of the present invention is to provide a method for increasing the production of bacteriocin 760 in vitro wherein a peptide having SEQ ID NO 7 is added to a culture of *Streptococcus cricetus* LWP 760 cells (NRRL B-30745).

Another object of the present invention is to provide a method for increasing the production of a bacteriocin by a producer cell line by further including an inducer cell line.

A still further object of the present invention is to provide a method for increasing the production of bacteriocin OR-7 by producer cell line *Lactobacillus* salivarius PVD-32 by further including inducer cell line *Lactobacillus crispatus* LWP 252 (NRRL B-30884).

A still further object of the present invention is to provide a method for increasing the production of bacteriocin 50-52 by producer cell line *Enterococcus faecium* LWP 50-52 by further including inducer cell line *Lactobacillus acidophilus* LWP 320 (NRRL B-30510).

A still further object of the present invention is to provide a method for increasing the production of bacteriocin 760 by producer cell line *Streptococcus* cricetus LWP 760 by further including inducer cell line *Lactobacillus acidophilus* LWP 320.

Further objects and advantages of the invention will become apparent from the following description.

Deposit of the Microorganisms

*Lactobacillus* salivarius, designated NRRL B-30514 (Strain PVD32) was deposited on Aug. 3, 2001. *Streptococcus* cricetus, designated NRRL B-30745 (Strain LWP 760), and *Enterococcus faecium* designated NRRL B-30746 (Strain LWP-50-52) were been deposited on May 3, 2004; and *Lactobacillus acidophilus*, designated NRRL B-30510 (Strain LWP 320) was deposited on Aug. 3, 2001. *Lactobacillus* crispatus, designated NRRL B-30884 (Strain LWP 252) was deposited on Nov. 4, 2005. All of the above strains have been deposited under the provisions of the Budapest Treaty, with U.S.D.A. Agricultural Research Service Patent Culture Collection (National Center for Agricultural Utilization Research, 1815 N. University Street, Peoria, Ill. 61604).

BRIEF DESCRIPTION OF THE DRAWINGS

The patent or application file contains at least one drawing executed in color. Copies of this patent or patent application publication with color drawing(s) will be provided b the Office upon request and payment of the necessary fee.

In FIG. 1A Lane 1-Molecular Mass Markers LMW Range 2,100-12,500 (Amersham Pharmacia Biotech): 2,100; 5,780; 8,400; 12,500 Da. The band in Lane 2 containing pure bacteriocin OR-7 corresponds to the antimicrobial activity, the zone of growth inhibition had a mass of about 5.5 kDa. The band in Lane 3 containing pure signal peptide from PVD-32 had a mass of about 2.5 kDa. In FIG. 1B, Lane 1 containing pure bacteriocin OR-7 which corresponds to the antimicrobial activity; the zone of growth inhibition had a pI of about 8.4. The band in Lane 2 which contains pure signal peptide form PVD-32 had a pI of about 7.9. Lane 3 contained pI standards (Protein Test Mixture, I Marker Proteins, Serva): 10.0, 9.2, 8.1, 6.9, 5.5, 4.3.

In FIG. 1A, Lane 1 shows Molecular Mass Markers LMW Range of about 2,100-12,500 (Amersham Pharmacia Biotech): 2,100; 5,780; 8,400; 12,500 Da. The band in Lane 2 containing pure bacteriocin 50-52 corresponds to the antimicrobial activity, the zone of growth inhibition had a mass of about 3.9 kDa. The band in Lane 3 containing pure signal peptide for LWP-50-52 had a mass of about 3.1 kDa. In FIG. 2B, the band in Lane 1 containing pure bacteriocin 50-52 corresponds to the antimicrobial activity; the zone of growth inhibition had a pI of about 8.4. The band in Lane 2 containing pure signal peptide from LWP-50-52 had a pI of about 8.1. Lane 3 contained pI standards (Protein Test Mixture, I Marker Proteins, Serva): 10.0, 8.1, 7.9, 6.4, 5.5, 4.3, 4.1, and 3.8.

In FIG. 3A, Lane 3 shows Molecular Mass Markers LMW Range of about 2,100-12,500 (Amersham Pharmacia Biotech): 2,100; 5,780; 8,400; 12,500 Da. The band in Lane 1 containing pure bacteriocin 760 corresponds to the antimicrobial activity; the zone of growth inhibition had a mass of about 5.5 kDa. The band in Lane 3 containing pure signal peptide form LWP 760 had a mass of about 2.1 kDa. In FIG. 3B, the band in Lane 1 containing pure bacteriocin 760 corresponds to the antimicrobial activity; the zone of growth inhibition had a pI of about 9.5. The band in Lane 2 containing pure signal peptide from LWP-760 had a pI of about 8.9. Lane 3 contained pI standards (Protein Test Mixture, I Marker Proteins, Serva): 10.0, 8.1, 7.9, 6.4, 5.5, 4.3, 4.1, and 3.8.

DETAILED DESCRIPTION OF THE INVENTION

Figure 1:
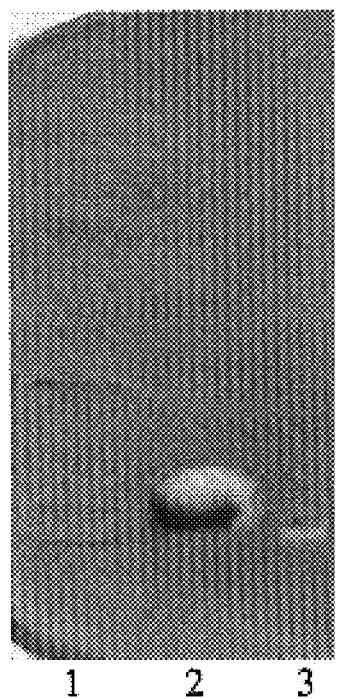
FIGS. 1A and 1B are photographs showing the direct detection of signal peptide and bacteriocin OR-7 after SDS-PAGE (A) and isoelectrofocusing (B). The gel was overlaid with *Campylobacter jejuni* to determine which band(s) corresponds to the antimicrobial activity, molecular weight, and isoelectric point.
Figure 1:
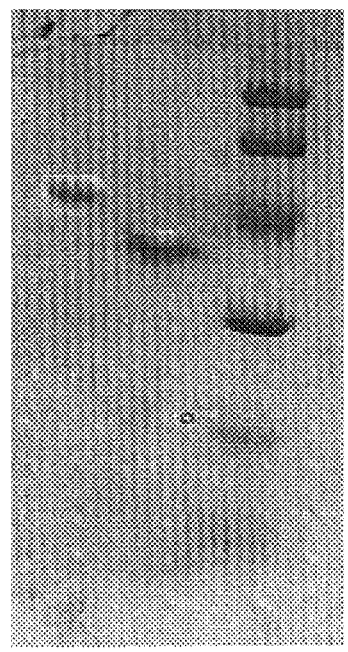

The importance of enteric infections in humans has been increasingly well recognized and the relationship of poultry contamination and human infection is well documented. The ability to diminish this health hazard by interventions at poultry processing plants is also well known. During boiler production and processing, fecal materials containing pathogens are transferred to meat and persist in the food processing kitchens.

Metabolites of competing organisms may contribute to the control of pathogens such as *Campylobacter jejuni* and *Salmonella*. *Lactobacillus* salivarius, designated NRRL B-30514 (Strain PVD32), *Streptococcus* cricetus, designated NRRL B-30745 (Strain LWP-760); and *Enterococcus faecium*, designated NRRL B-30746 (Strain LWP-50-52) produce novel bacteriocins which are the subject of pending U.S. patent application Ser. No. 10/644,927, filed Aug. 21, 2003 and pending U.S. patent application Ser. No. 10/426, 688, filed May 1, 2003, both herein incorporated by reference in their entirety. These strains also produce novel peptides which stimulate the strains to produce higher amounts of bacteriocins in vitro.

The present invention provides for novel signal peptides and the strains producing the peptides, novel inducer strains, amino acid sequences, and methods for using the novel peptides and inducer strains.

*Lactobacillus* salivarius, PVD-32, (NRRL B-30514) produces signal peptide SEQ ID NO 3. It is an aerobe with gram-positive bacilli and is capable of growth at about 37° C. The strain grows on nutrient and plate count agar producing irregular-shaped edges. The colonies are white in color and are about 3 mm in diameter after aerophilic cultivation for about 24 hours at about 37° C.

*Enterococcus faecium*, LWP 50-52 (NRRL B-30746) produces signal peptide SEQ ID NO 5. It is a facultative aerobe with gram-positive cocci and is capable of growth at about 37° C. The strain grows on nutrient or plate count agar producing irregular-shaped edges. The colonies are grey in color and are about 2 mm in diameter after microaerophilic cultivation at about 37° C. for about 24 hours.

*Streptococcus* cricetus, LWP-760 (NRRL B-30745) produces signal peptide SEQ ID NO 7. It is a facultative aerobe with gram-positive cocci and is capable of growth at about 37° C. The strain grows on nutrient or plate count agar producing regular-shaped edges. The colonies are grey in color and are about 1 mm in diameter after microaerophilic cultivation for about 24 hours at about 37° C.

*Lactobacillus acidophilus*, LWP 320 (NRRL B-30510), is an inducer strain which is a facultative aerobe with gram-positive cocci and is capable of growth at about 37° C. The strain grows on nutrient or plate count agar producing irregular-shaped edges. The colonies are white in color and are about 3 mm in diameter after microaerophilic cultivation for about 24 hours at about 37° C.

*Lactobacillus crispatus* LWP 252 (NRRL B-30884) is an inducer strain which is an aerobe with gram-positive cocci and is capable of growth at about 37° C. The strain grows on nutrient or plate count agar producing regular-shaped edges. The colonies are grey in color and are about 1 mm in diameter after aerophilic cultivation for about 24 hours at about 37° C.

Signal peptides from strains producing bacteriocins were isolated and purified. Cells of producers mainly secrete bacteriocins of Class II through the ABC transportation system (Haverstein et al., Mol. Microbiol., Volume 16, 229-240, 1995; Gajic et al., J. Biol. Chem., Volume 36, 34291-34298, 2003). Secretion of some bacteriocins of this class takes place due to signal peptides which are activated by Sec translocase located on cytoplasmic membranes (Cintas et al., Appl. Environ. Microbiol., Volume 63, 4321-4330, 1997; Doi et al., J. Biosci. Bioeng., Volume 93, 434-436, 2002; Leer et al., Microbiology, Volume 141, 1629-1635, 1995; Martinez et al., Microbiology, Volume 145, 3155-3161, 1999; Tomita et al., J. Bacteriol., Volume 178, 3585-3593, 1999; Worobo et al., J. Bacteriol., Volume 177, 3143-3149, 1995; and Herranz et al., J. Appl. Environ. Microbiol., Volume 71 (4), 1959-1963, 2005). Another function of signal peptides is likely associated with the bacterial phenomenon "quorum sensing" (De Kievit et al., Infection and Immunity, Volume 68(9), 4839-4849, 2000; Dunny et al., In: *Microbial Signaling and Communication*, England et al. (eds.), University Press, Cambridge, United Kingdom, 117-138, 1999; Dunning and Leonard, Annu. Rev. Microbiol., Volume 51, 527-564, 1997; and Kleerebezem et al., Mol. Microbiol., Volume 24, 895-904, 1997). A signal peptide either alone or in a complex with metabolites of an inducing strain, activates histidine protein kinase in the producer, thereby increasing bacteriocin production. To obtain maximum peptide production, cells that produce signal peptides, such as PVD 32, LWP 50-52, and LWP 760, were cultured for about 2-10 hours in M9 broth supplemented with an amino acid selected from the group consisting of phenylalanine, tryptophan, alanine, and mixtures thereof. A preferred embodiment of the present invention includes amino acid amounts in the range of approximately 0.01% to approximately 0.1% for each amino acid included in the composition. A medium of approximately 10% *Brucella* broth results in production of a signal peptide at a lower concentration.

The signal peptide is isolated from culture supernatant using ammonium sulfate precipitation followed by (1) gel filtration using Superose 12 High Resolution chromatography; and (2) Octyl-Sepharose 6B Fast Flow hydrophobic interaction chromatography.

The signal peptides of the present invention are used to increase the production of bacteriocins in vitro by producer cells when in the presence of an inducer bacteria. The signal peptide can be added any time during culture of the inducer and producer bacteria. Given the present Detailed Description of the invention, one of ordinary skill in the art could readily determine when to add the signal peptide to achieve high levels of bacteriocin production as compared to bacteriocin production in cultures containing only the peptide and producer or only the producer and inducer bacteria.

The antagonistic activity of the bacteriocins produced when using the signal peptide and an inducer strain of bacteria against *C. jejuni* and *S. enteritidis* was assessed using a Spot Test. The steps included taking various concentrations of pure preparation (µg/ml) of the bacteriocin in approximately 10 microliters of volume plated onto blood-supplemented *Campylobacter* agar or Nutrient agar (MPA or Meta Peptone Agar) previously seeded with cells of target bacteria. Plates containing cultures of *C. jejuni* were grown at about 42° C., under microaerobic conditions. Plates containing *S. enteritidis* were grown at about 37° C. under aerobic conditions. Activity of the bacteriocin was expressed in arbitrary units (AU) per one milliliter of the preparation at which a visible zone of inhibition of the growth of culture appears (Henderson et al., Archives of Biochemistry and Biophysics, Volume 295, 5-12, 1992; herein incorporated by reference). Specific activity can also expressed as arbitrary units per milligram of pure bacteriocin.

Signal peptides of the present invention include any peptide with a carboxy terminal sequence of VKGLT (SEQ ID NO 1) produced by a bacteriocin-secreting bacteria that increases bacteriocin production when added to a culture including a producer bacteria or a producer bacteria and an inducer bacteria.

For purposes of the present invention an inducer bacteria is defined as any bacteria which, when cultured with a bacteriocin-producing bacteria-a producer bacteria-along with the producer's signal peptide, increases the production of bacteriocin over that of a culture containing only the producer bacteria and it's signal peptide.

For purposes of the present invention, the term "peptide" means a compound of at least two or more amino acids or amino acid analogs. The amino acids or amino acid analogs may be linked by peptide bonds. In another embodiment, the amino acids may be linked by other bonds, e.g. ester, ether, etc. Peptides can be in any structural configuration including linear, branched, or cyclic configurations. As used herein, the term "amino acids" refers to either natural or synthetic amino acids, including both the D or L optical isomers and amino acid analogs.

Peptide derivatives and analogs of the present invention include, but are not limited to, those containing as a primary amino acid sequence, all or part of the amino acid sequence of the peptide including altered sequences in which functionally equivalent amino acid residues are substituted for residues within the sequence resulting in conservative amino acid substitution.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan, and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Such alterations will not be expected to significantly affect apparent molecular weight as determined by polyacrylamide gel electrophoresis or isoelectric point. Non-conservative amino acid substitutions may also be introduced to substitute an amino acid with a particularly preferable property. For example, Cys may be introduced at a potential site for disulfide bridges with another Cys. Pro may be introduced because of its particularly planar structure.

The peptides of the present invention can be chemically synthesized. Synthetic peptides can be prepared using the well known techniques of solid phase, liquid phase, or peptide condensation techniques, or any combination thereof, and can include natural and/or synthetic amino acids. Amino acids used for peptide synthesis may be standard Boc($N^\alpha$-amino protected $N^\alpha$-t-butyloxycarbonyl) amino acid resin with the standard deprotecting, neutralization, coupling, and wash protocols of the original solid phase procedure of Merrifield (J. Am. Chem. Soc., Volume 85, 2154, 1963), or the base-labile $N^\alpha$-amino protected 9-fluorenylmethoxycarbonyl (Fmoc) amino acid (Carpino and Han, J. Org. Chem., Volume 37, 3403-3409, 1972). In addition, the method of the present invention can be used with other $N^\alpha$-protecting groups that are familiar to those skilled in the art. Solid phase peptide synthesis may be accomplished by techniques within the ordinary skill in the art (See for example, Stewart and Young, Solid Phase Synthesis, Second Edition, Pierce Chemical Company, Rockford, Ill., 1984; Fields and Noble, Int J. Pept. Protein Res., Volume 35, 161-214, 1990), or by using automated synthesizers.

The following examples are intended only to further illustrate the invention and are not intended to limit the scope of the invention as defined by the claims.

EXAMPLE 1

Cells of strains *Enterococcus faecium* LWP50-52, *Streptococcus cricetus* LWP-760, and *Lactobacillus* salivarius PVD-32 were plated into flasks containing about 300 ml of the following media: *Brucella* broth, 10% *Brucella* broth, or M9 supplemented with amino acids as indicated below in Table 1. Flasks were cultivated by shaking at about 37° C. for about 2,4,6 and 8 hours. The speed of rotation was approximately 120 rpm. Aliquots of the culture fluid were centrifuged at about 6000×g for about 15 minutes at about −4° C. Peptides were isolated by sedimentation of proteins with about a 40% solution of $(NH_4)_2SO_4$ at about 4° C. for approximately 24 hours, followed by gel filtration using Superose-12 High Resolution chromatography with selection of low-molecular weight fractions. These fractions were applied to a Octyl-Sepharose 6 B Fast Flow hydrophobic interaction chromatography column and proteins were eluted with about a 0.4-0.9 M $K_2HPO$ in 0.1 M Tris buffer, pH 5.1 gradient. Results are present below in Table 1. As seen from Table 1, the peptides isolated from producers PVD 32, LWP 50-52 and LWP 760 are low-molecular-weight and accumulate mainly in cultures containing starvation media (M9+indicated amino acids).

TABLE 1

Isolation and purification of inducer peptides from strains PVD-32, LWP-50-52, and LWP-760.

| Cultivation | Time in Cultivation (Hours) | | | |
|---|---|---|---|---|
| | 2 | 4 | 6 | 8 |
| PVD-32 | | | | |
| Brucella Broth | 0 | 0 | 0 | 0 |
| 10% Brucella Broth | 0 | 0 | Peptide, m.w. 2.5 kDa 0.4 mg/ml, volume = 1 ml | 0 |
| M9 + 0.03% Phenylalanine 0.07% Tryptophan | 0 | Peptide m.w. = 2.5 kDa 0.2 mg/ml, Volume = 1 ml | Peptide, m.w. 2.5 kDa 0.9 mg/ml Volume = 1 ml | 0 |
| LWP-50-52 | | | | |
| Brucella Broth | 0 | 0 | 0 | 0 |
| 10% Brucella Broth | 0 | Peptide, m.w. 3.1 kDa 0.5 mg/ml, Volume = 1 ml | 0 | 0 |
| M-9, 0.05% Tryptophan | 0 | 0 | Peptide, m.w. 3.1 kDa 1.3 mg.ml, Volume = 1 ml | Peptide, m.w. 3.1 kDa 0.1 mg/ml, Volume = 1 ml |

TABLE 1-continued

Isolation and purification of inducer peptides from strains PVD-32, LWP-50-52, and LWP-760.

| Cultivation | Time in Cultivation (Hours) | | | |
|---|---|---|---|---|
| | 2 | 4 | 6 | 8 |
| | | | LWP-760 | |
| Brucella Broth | 0 | 0 | 0 | 0 |
| 10% Brucella Broth | 0 | 0 | Peptide, m.w. 2.1 kDa 2.1 mg/ml, volume = 1 ml | 0 |
| M-9 0.02% alanine 0.07% phenylalanine | 0 | 0 | Peptide m.w. 2.1 kDa 2.8 mg/ml, volume = 1 ml | 0 |

The isolated signal peptide for PVD-32 possessed weak antagonistic activity against *C. jejuni* and *S. enteritidis*, as determined in a spot test. Its activity was about 200 AU/ml and its molecular weight was about 2.5 kDa, as determined by SDS-PAGE electrophoresis. The isoelectric point (pI) was about 7.9 (FIGS. 1A and 1B).

Figure 2:
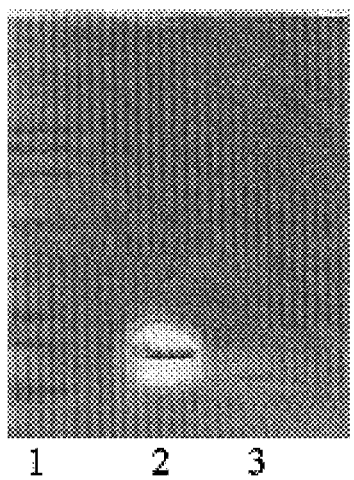
FIGS. 2A and 2B are photographs showing direct detection of signal peptide and bacteriocin 50-52 after SDS-PAGE (A) and isoelectrofocusing (B). The gels were overlaid with *Campylobacter jejuni* to determine which band(s) corresponds to the antimicrobial activity, molecular weight, and isoelectric point.
Figure 2:
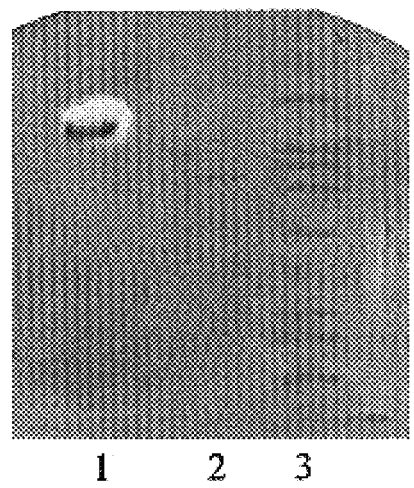

The isolated signal peptide for LWP50-52 did not possess antagonistic activity against *C. jejuni* and *S. enteritidis*, as determined by a Spot Test. Its molecular weight was about 3.1 kDa as measured by SDS-PAGE and the isoelectric point (pI) was about 8.1 (FIGS. 2A and 2B).

Figure 3:
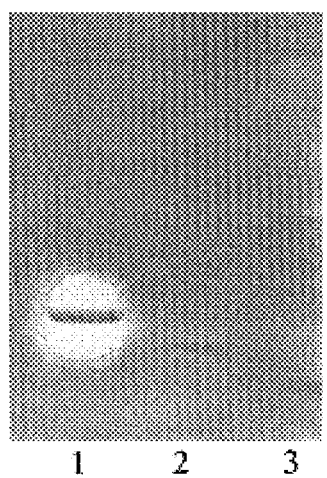
FIGS. 3A and 3B are photographs showing the direct detection of signal peptide and bacteriocin 760 after SDS-PAGE(A) and isoelectrofocusing (B). The gels are overlaid with *Campylobacter jejuni* to determine which band(s) corresponds to the antimicrobial activity, molecular weight, and isoelectric point.
Figure 3:
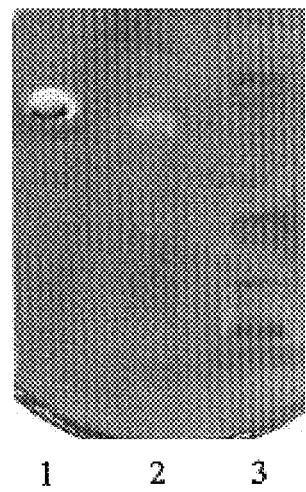

The isolated signal peptide for LWP-760 did not possess antagonistic activity toward *C. jejuni* and *S. enteritidis* as determined by a Spot Test. Its molecular weight was about 2.1 kDa as determined by SDS-PAGE electrophoresis and its isoelectric point was about 8.9 (FIGS. 3A and 3B).

EXAMPLE 2

To determine the efficacy of the signal peptide isolated from PVD-32 cells in the production of bacteriocin OR-7, PVD-32 cells were cultured in flasks with about 300 ml of approximately 10% *Brucella* Broth. About 1 ml of a PVD-32 cell suspension containing approximately 109 CFU/ml was added to the broth, approximately 1 ml of inducer strain LWP 252 cell suspension containing approximately 109 CFU/ml, and approximately 0.10 mg/ml, 0.01 mg/ml, or 0.001 mg/ml of PVD 32 signal peptide were also added. A control sample did not contain the signal peptide. Some samples contained the different concentrations of signal peptide and the producer strain, with no inducer strain. Two samples contained either 0.1 mg/ml signal peptide from LWP 760 or 0.1 mg/ml signal peptide from LWP-50-52 with both the inducer and the producer strains. The flasks were cultured at about 37° C. for approximately 14 hours using a stirring speed of approximately 120 rpm. The results are summarized below in Table 2.

At the end of 14 hours the supernatant from the cultures was placed into 500 ml centrifuge flasks with about one milliliter of regenerated Sepharose SP Fast Flow (v/v 500:1). This was incubated for approximately 1 hour at room temperature with stirring. The suspension was then washed with about 100 ml of a 0.2 M TRIS-HCl buffer pH approximately 6.4. The bacteriocins were eluted by centrifugation with about 100 ml of approximately 0.2 M $K_2HPO_4$, pH of about 5.8 at about 7,000×g for approximately 10 minutes. Antagonistic activity of the bacteriocin fractions against *C. jejuni* and *S. enteritidis* was assessed using a Spot Test as described above. The level of purity of the bacteriocin fractions was determined by SDS-PAGE. The isoelectric points of the fractions were determined by isoelectric focusing. Concentrations of protein for all bacteriocin fractions were determined at 215 nm using a spectrophotometer. The results are presented in Table 2 below.

As seen in Table 2, cultivation of PVD-32 (Producer) with LWP-252 (inducer) in the presence of about 0.01 mg of the purified signal peptide from PVD-32 increases the yield of bacteriocin OR-7 up to about 214.5 mg from one liter of culture fluid. The addition of signal peptides isolated from strains LWP 50-52 and LWP 760 does not increase the yield of bacteriocin OR-7 versus the control. This points to the fact that the signal peptide is strongly specific toward the producer. The synthesis of the bacteriocin increases when the signal peptide, producer, and inducer are simultaneously introduced into the culture fluid.

To assess the effect of the signal peptide on bacteriocin production under scaled-up cultivation, producing and inducing strains were grown in a bioreactor with the approximately six liters of culture fluid. The ratio of concentrations of cultures and the signal peptide was 109 CFU/ml of PVD-32 (producer strain), $10^9$ CFU/ml LWP-252 (inducer strain), and 0.01 mg/ml of purified signal peptide from PVD-32. Bacteriocin OR-7 was isolated after approximately 8, 10, 12, and 14 hours of cultivation. See Table 3. The scheme of purification is as described above. Experiments were repeated three times.

TABLE 2

Influence of signal peptide isolated from PVD-32 on bacteriocin OR-7 production.

| Experimental Conditions | Fraction Volume, ml | Protein concentration Mg/ml | Activity AU/ml | Specific Activity AU/mg | mg protein/ liter | Protein increase vs. control |
|---|---|---|---|---|---|---|
| 10% B-B, PVD-32 LWP-252 Control | 100 | 0.2 | 409,600 | 2,048,000 | 66 | 1 |

TABLE 2-continued

Influence of signal peptide isolated from PVD-32 on bacteriocin OR-7 production.

| Experimental Conditions | Fraction Volume, ml | Protein concentration Mg/ml | Activity AU/ml | Specific Activity AU/mg | mg protein/ liter | Protein increase vs. control |
|---|---|---|---|---|---|---|
| 10% B-B, PVD32, PVD-32 Signal Peptide-0.1 mg | 100 | 0.18 | 102,400 | 568,888 | 59.4 | 0.9 |
| 10% B-B, PVD-32, PVD-32 Signal Peptide-0.01 mg | 100 | 0.2 | 204,800 | 1,024,000 | 66 | 1 |
| 10% B-B, PVD-32, PVD-32 Signal Peptide-0.001 mg | 100 | 0.2 | 204,800 | 1,024,000 | 66 | 1 |
| 10% B-B, PVD-32, LWP-252, PVD-32 Signal Peptide-0.1 mg | 100 | 0.22 | 409,600 | 1,861,818 | 72.6 | 1.1 |
| 10% B-B, PVD-32, LWP-252, PVD-32 Signal Peptide-0.01 mg | 100 | 0.65 | 1,638,400 | 2,520,615 | 214.5 | 3.25 |
| 10% B-B, PVD-32, LWP-252, PVD-32 Signal Peptide-0.001 mg | 100 | 0.22 | 409,600 | 1,861,818 | 72.6 | 1.1 |
| 10% B-B, PVD-32, LWP-252, LWP 50-52 Signal Peptide-0.1 mg | 100 | 0.17 | 51,200 | 301,176 | 56.1 | 0.85 |
| 10% B-B, PVD-32, LWP-252, LWP 760 Signal Peptide-0.1 mg | 100 | 0.19 | 102,400 | 538,947 | 62.7 | 0.95 |

TABLE 3

Cultivation of producer strain PVD-32 and inducer strain LWP-252 in the presence of the PVD-32 Signal Peptide under scaled up conditions.

| Experimental Conditions | Volume of Fraction ml | Concentration of Protein mg/ml | Activity AU/ml | Specific Activity AU/mg | Amount of Protein produced in One liter mg | Increase in Amount of protein vs. control |
|---|---|---|---|---|---|---|
| Control | 900 | 0.5 | 512,000 | 1,024,000 | 75 | 1 |
| PVD-32, LWP-252, 0.2 mg PVD-32 Signal Peptide | 900 | 1.5 | 3,276,800 | 2,184,533 | 225 | 3 |

Control: V-61 bioreactor, 10% Brucella Broth, PVD-32, LWP252, at pH 6.9, 37° C., 150 r.p.m., 14 hours cultivation.
Signal Peptide: V-61 reactor, 10% Brucella Broth, PVD-32, LWP252, PVD-32 Signal peptide-0.2 mg, pH 6.9, 37° C., 150 r.p.m., 14 hours cultivation.

The simultaneous culture of PVD-32 (Producing Strain) and LWP-252 (Inducing Strain) in the presence of the specific signal peptide isolated from PVD-32 allows for the production of about 214-225 milligrams of bacteriocin OR-7 per liter of culture fluid.

EXAMPLE 3

To determine the efficacy of the signal peptide isolated from LWP 50-52 in the production of bacteriocin 50-52, LWP 50-52 was cultured at 37° C. as described above in Example 2. About 1 ml of a LWP 50-52 cell suspension containing approximately $10^9$ CFU/ml was added to 10% Brucella broth, approximately $10^9$ CFU/ml of inducer strain LWP-320 was add to the broth, and approximately 0.10 mg/ml, 0.01 mg/ml, or 0.001 mg/ml of LWP 50-52 signal peptide were also added. A control sample did not contain the signal peptide. Some samples contained the different concentrations of signal peptide and the producer strain with no inducer strain. Two samples contained either 0.10 mg/ml of signal peptide from LWP 760 or 0.10 mg/ml signal peptide from PVD-32 with both the inducer and the producer strains. The flasks were cultured at about 37° C. for approximately 14 hours using a stirring speed of approximately 120 RPM. The results are summarized below in Table 4.

Isolation of bacteriocin 50-52 involved two steps: (1) the isolation of bacteriocin from the supernatant of the culture fluid and (2) the isolation of bacteriocin from the precipitate of cells of both the inducing and the producing strains. In step 1, the cultures were harvested and separated by centrifugation at about 10,000×g for about 15 minutes to precipitate the cells. The supernatant was applied to an Octyl Sepharose 4 Fast Flow column to recover the bacteriocin using an elution buffer of about 20 mM $K_2HPO_4$ buffer, pH approximately 7.0. The cell precipitate from step 2 was suspended in phosphate buffer with about 0.7% NaCl, pH approximately 5.6 (elution buffer) and the suspension was mixed and incubated for about 20 minutes. After incubation, the suspension was centrifuged at about 10,000×g for about 15 minutes. The bacteriocin was isolated from the supernatant using ion-exchange chromatography on Superose SP Fast Flow using an elution buffer containing about 10 mM Tris HCl and about 125 mM NaCl, pH approximately 7.5. Antagonistic activities of the bacteriocin fractions against *C. jejuni* and *S. enteritidis* were assessed in a spot-test. The level of purity of bacteriocins was determined by SDS-PAGE. The isoelectric points of the fractions were determined using isoelectricfocusing. Concentrations of protein for all bacteriocin fractions were determined at approximately 215 nm using a spectrophotometric method.

TABLE 4

Influence of signal peptide isolated from LWP 50-52 on bacteriocin 50-52 production.

| Experimental Conditions | Fraction Volume, ml | Protein Concentration mg/ml | Activity AU/ml | Specific Activity AU/mg | mg protein/ liter | Protein increase vs. Control |
|---|---|---|---|---|---|---|
| 10% B-B, LWP 50-52, LWP-320 (control) | 100 | 0.25 | 819,200 | 3,276,800 | 82.5 | 1 |
| 10% B-B, LWP 50-52, LWP 50-52 Signal Peptide: 0.1 mg/ml | 100 | 0.25 | 819,200 | 3,276,800 | 82.5 | 1 |
| 10% B-B, LWP 50-52, LWP 50-52 Signal Peptide: 0.1 mg/ml added after about 2 hours of cultivation | 100 | 0.27 | 819,200 | 3,034,074 | 89.1 | 1.08 |
| 10% B-B, LWP 50-52, LWP 50-52 Signal Peptide: 0.10 mg/ml added after about 4 hours of cultivation | 100 | 0.27 | 819,200 | 3,034,074 | 89.1 | 1.08 |
| 10% B-B, LWP 50-52, LWP 50-52 Signal Peptide: 0.10 mg/ml added after about 6 hours of cultivation | 100 | 0.26 | 819,200 | 3,150,769 | 85.8 | 1.04 |
| 10% B-B, LWP 50-52, LWP 50-52 Signal Peptide 0.01 mg/ml | 100 | 0.27 | 819,200 | 3,034,074 | 89.1 | 1.08 |
| 10% B-B, LWP 50-52, LWP 50-52 Signal Peptide: 0.01 mg/ml added after about 2 hours of cultivation | 100 | 0.31 | 819,200 | 2,642,580 | 102.3 | 1.24 |
| 10% B-B, LWP 50-52, LWP 50-52 Signal Peptide: 0.01 mg.ml added after about 4 hours of cultivation | 100 | 0.27 | 819,200 | 3,034,074 | 89.1 | 1.08 |
| 10% B-B, LWP 50-52, LWP 50-52 Signal Peptide: 0.01 mg.ml added after about 6 hours of cultivation | 100 | 0.27 | 819,200 | 3,034,074 | 89.1 | 1.08 |
| 10% B-B, LWP 50-52, LWP 50-52 Signal Peptide: 0.001 mg/ml | 100 | 0.25 | 819,200 | 3,276,800 | 82.5 | 1 |
| 10% B-B, LWP 50-52, LWP 50-52 Signal Peptide: 0.001 mg/ml added after about 2 hours of cultivation | 100 | 0.25 | 819,200 | 3,276,800 | 82.5 | 1 |
| 10% B-B, LWP 50-52, LWP 50-52 Signal Peptide: 0.001 mg/ml added after about 4 hours of cultivation | 100 | 0.25 | 819,200 | 3,276,800 | 82.5 | 1 |
| 10% B-B, LWP 50-52, LWP 50-52 Signal Peptide: 0.001 mg/ml added after about 6 hours of cultivation | 100 | 0.25 | 819,200 | 3,276,800 | 82.5 | 1 |
| 10% B-B, LWP 50-52, LWP 320 Signal Peptide: 0.1 mg/ml | 100 | 0.25 | 819,200 | 3,276,800 | 82.5 | 1 |
| 10% B-B, LWP 50-52, LWP 320 Signal Peptide: 0.1 mg/ml added after about 2 hours of cultivation | 100 | 0.25 | 819,200 | 3,276,800 | 82.5 | 1 |
| 10% B-B, LWP 50-52, LWP 320 Signal Peptide: 0.1 mg/ml added after about 4 hours of cultivation | 100 | 0.25 | 819,200 | 3,276,800 | 82.5 | 1 |
| 10% B-B, LWP 50-52, LWP 320 Signal Peptide: 0.1 mg/ml added after about 6 hours of cultivation | 100 | 0.25 | 819,200 | 3,276,800 | 82.5 | 1 |
| 10% B-B, LWP 50-52, LWP 320 Signal Peptide: 0.01 mg/ml | 100 | 1.0 | 1,638,400 | 1,638,400 | 330.0 | 4 |
| 10% B-B, LWP 50-52, LWP 320 Signal Peptide: 0.01 mg/ml added after about 2 hours of cultivation | 100 | 1.07 | 3,276,800 | 3,062,429 | 353.1 | 4.28 |
| 10% B-B, LWP 50-52, LWP 320 Signal Peptide: 0.01 mg/ml added after about 4 hours of cultivation | 100 | 1.0 | 1,638,400 | 1,638,400 | 330.0 | 4 |
| 10% B-B, LWP 50-52. LWP 320 Signal Peptide: 0.01 mg/ml added after about 6 hours of cultivation | 100 | 1.0 | 1,638,400 | 1,638,400 | 330.0 | 4 |
| 10% B-B, LWP 50-52. LWP 320 Signal Peptide: 0.001 mg/ml | 100 | 0.25 | 819,200 | 3,276,800 | 82.5 | 1 |
| 10% B-B, LWP 50-52. LWP 320 Signal Peptide: 0.001 mg/ml added after about 2 hours of cultivation | 100 | 0.25 | 819,200 | 3,276,800 | 82.5 | 1 |
| 10% B-B, LWP 50-52. LWP 320 Signal Peptide: 0.001 mg/ml added after about 4 hours of cultivation | 100 | 0.25 | 819,200 | 3,276,800 | 82.5 | 1 |
| 10% B-B, LWP 50-52. LWP 320 Signal Peptide: 0.001 mg/ml added after about 6 hours of cultivation | 100 | 0.25 | 819,200 | 3,276,800 | 82.5 | 1 |
| 10% B-B, LWP 50-52. LWP 320, LWP 760 Signal Peptide: 0.1 mg/ml added | 100 | 0.25 | 819,200 | 3,276,800 | 82.5 | 1 |
| 10% B-B, LWP 50-52. LWP 320, PVD-32 Signal Peptide: 0.1 mg/ml added | 100 | 0.25 | 819,200 | 3,276,800 | 82.5 | 1 |

As seen from Table 4, the simultaneous cultivation of LWP 50-52 (Producer Strain) and LWP 320 (Inducer Strain) in the presence of approximately 0.01 mg/ml of the signal peptide from LWP 50-52 for about 8 hours increases the yield of bacteriocin 50-52 up to about 353.1 mg from 1 liter of the culture fluid. The addition of signal peptides isolated from PVD-32 and LWP 760 did not increase the yield of bacteriocin 50-52 versus the control. It should be noted that the synthesis of the bacteriocin increases maximally if the signal peptide is introduced into the culture fluid approximately 2 hours after the beginning of the cultivation with a total cultivation time of about 12 hours.

To evaluate influence of the signal peptide on bacteriocin production under scaled-up cultivation, producing and inducing strains were grown in a V-6 liter bioreactor containing about 6 liters of medium. The ratio of concentrations of cultures and the signal peptide was maintained as in Table 5 for the conditions of 10% Brucella Broth, LWP 50-52, LWP 320, 0.01 mg/ml of LWP 50-52 signal peptide added after about 2 hours of cultivation. Isolation of bacteriocin 50-52 was performed at about 8, 10, 12, and 14 hours of cultivation as described above. The control contained 10% Brucella Broth, LWP 50-52, LWP-320, at a pH of approximately 6.9, at about 37° C., and about 150 rpm. The bacteriocin 50-52 was isolated after about 12 hours of cultivation. For the second condition, the conditions were the same except that approximately 0.22 mg of LWP 50-52 signal peptide was added after 2 hours of cultivation. Results are shown below in Table 5. Each condition was repeated three times.

was added either at the time of cultivation or at about 2,4, or 6 hours after the start of cultivation. For another set of variables, about 1 ml of a LWP-760 cell suspension containing approximately $10^9$ CFU/ml was added to about 10% Brucella broth, approximately 1 ml of an inducer strain LWP-320 cell suspension containing approximately $10^9$ CFU/ml was added to the broth, and approximately 1 ml of an approximately 0.1 mg/ml, 0.01 mg/ml, or 0.001 mg/ml LWP-760 signal peptide preparation was added either at the time of cultivation or at about 2,4, or 6 hours after the start of cultivation. The next set of conditions included about 1 ml of a LWP-760 cell suspension containing approximately $10^9$ CFU/ml was added to about 10% Brucella broth, approximately 1 ml of an inducer strain LWP-320 cell suspension containing approximately $10^9$ CFU/ml was added to the broth and about 1 ml of an approximately 0.1 mg/ml preparation of purified LWP-50-52 signal peptide or purified PVD-32 signal-peptide was added at the start of cultivation. The control contained about 1 ml of a LWP-760 cell suspension containing approximately $10^9$ CFU/ml and approximately 1 ml of an inducer strain LWP-320 cell suspension containing approximately $10^9$ CFU/ml in 10% Brucella broth.

Bacteriocin 760 was isolated using centrifugation to separate cell and culture fluid at about 10,000×g for about 15 minutes. The supernatant was applied to an Octyl Sepharose 4 Fast Flow column to recover bacteriocin and eluted with about a 15 mM $K_2HPO_4$ elution buffer at a pH of about 6.3. The cell pellet was suspended in phosphate buffer containing approximately 0.7% NaCl, pH about 5.6 (eluting buffer) and

TABLE 5

Cultivation of Producer Strain LWP 50-52 and Inducer Strain LWP-320 in the presence of LWP 50-52 Signal Peptide.

| Experimental Conditions | Fraction Volume ml | Protein Concentration mg/ml | Activity AU/ml | Specific Activity AU/mg | Amount of Protein/liter of medium mg | Increase in the amount of protein vs. control |
|---|---|---|---|---|---|---|
| Control | 900 | 0.6 | 1,638,400 | 2,730,667 | 90 | 1 |
| 0.22 mg LWP 50-52 signal Peptide added after 2 hours of cultivation | 900 | 2.4 | 6,553,600 | 2,730,665 | 360 | 4 |

The cultivation of LWP 50-52 with LWP-320 in the presence of the LWP 50-52 signal peptide introduced about 2 hours after the beginning of cultivation, results in the production of about 360 mg/liter of bacteriocin 50-52 after approximately 12 hours cultivation.

EXAMPLE 4

To determine the efficacy of the signal peptide isolated from LWP-760 for production of bacteriocin 760, LWP-760 was cultured at about 37° C. as described above in Example 2. About 1 ml of a LWP-760 cell suspension containing approximately $10^9$ CFU/ml was added to about 10% Brucella broth, and approximately 1 ml of a 0.1 mg/ml, 0.01 mg/ml, or 0.001 mg/ml LWP-760 signal peptide preparation the suspension was mixed and incubated for about 20 minutes. After the incubation period, the suspension was centrifuged at about 10,000×g for about 15 minutes. The supernatant was applied to a Superose SP Fast Flow column to isolate the bacteriocin using an elution buffer containing about 25 mM Tris HCl and about 90 mM NaCl at a pH of about 6.4. Antagonistic activities of the bacteriocin fractions against C. jejuni and S. enteritidis were assessed in a Spot Test as described above. The level of purity of bacteriocin 760 was determined by SDS-PAGE. The isoelectric point was determined using isoelectric focusing. Concentrations of the protein were determined at about 215 nm using a spectrophotometric method. Results are presented below in Table 6.

TABLE 6

Influence of LWP-760 Signal Peptide on the Production of Bacteriocin 760.

| Experimental Conditions | Fraction Volume ml | Protein Concentration mg/ml | Activity AU/ml | Specific Activity Au/mg | Protein Produced from 1 liter Culture Fluid Mg | Increase in amount of protein vs. control |
|---|---|---|---|---|---|---|
| Control LWP 760 LWP 320 | 100 | 0.3 | 1,638,840 | 5,462,666 | 99 | 1 |
| LWP 760 + 0.1 mg LWP 760 Signal Peptide | 100 | 0.31 | 1,638,840 | 5,286,580 | 102.3 | 1.03 |
| LWP 760 + 0.1 mg LWP 760 Signal Peptide added after about 2 hours of cultivation | 100 | 0.31 | 1,638,840 | 5,286,580 | 102.3 | 1.03 |
| LWP 760 + 0.1 mg LWP 760 Signal Peptide added after about 4 hours of cultivation | 100 | 0.31 | ,638,840 | 5,286,580 | 102.3 | 1.03 |
| LWP 760 + 0.1 mg LWP 760 Signal Peptide add after about 6 hours of cultivation | 100 | 0.31 | 1,638,840 | 5,286,580 | 102.3 | 1.03 |
| LWP 760 + 0.01 mg LWP 760 Signal Peptide | 100 | 0.3 | 1,638,840 | 5,462,666 | 99 | 1 |
| LWP 760 + 0.01 mg LWP 760 Signal Peptide added after about 2 hours of cultivation | 100 | 0.30 | 1,638,840 | 5,462,666 | 99 | 1 |
| LWP 760 + 0.01 mg LWP 760 Signal Peptide added after about 4 hours of cultivation | 100 | 0.30 | 1,638,840 | 5,462,666 | 99 | 1 |
| LWP 760 + 0.01 mg LWP 760 Signal Peptide added after about 6 hours of cultivation | 100 | 0.30 | 1,638,840 | 5,462,666 | 99 | 1 |
| LWP 760 + 0.001 mg LWP 760 Signal Peptide | 100 | 0.30 | 1,638,840 | 5,462,666 | 99 | 1 |
| LWP 760 + 0.001 mg LWP 760 Signal Peptide added after about 2 hours of cultivation | 100 | 0.30 | 1,638,840 | 5,462,666 | 99 | 1 |
| LWP 760 + 0.001 mg LWP 760 Signal Peptide added after about 4 hours of cultivation | 100 | 0.30 | 1,638,840 | 5,462,666 | 99 | 1 |
| LWP 760 + 0.001 mg LWP 760 Signal Peptide added after about 6 hours of cultivation | 100 | 0.30 | 1,638,840 | 5,462,666 | 99 | 1 |
| LWP 760 + LWP 320 + 0.1 mg LWP 760 Signal Peptide | 100 | 0.28 | 1,638,840 | 5,853,000 | 92.4 | 0.9 |
| LWP 760 + LWP 320 + 0.1 mg LWP 760 Signal Peptide added after about 2 hours of cultivation | 100 | 0.35 | 1,638,840 | 4,682,400 | 115.5 | 1.16 |
| LWP 760 + LWP 320 + 0.1 mg LWP 760 Signal Peptide added after about 4 hours of cultivation | 100 | 0.35 | 1,638,840 | 4,682,400 | 115.5 | 1.16 |
| LWP 760 + LWP 320 + 0.1 mg LWP 760 Signal Peptide added after about 6 hours of cultivation | 100 | 0.35 | 1,638,840 | 4,682,400 | 115.5 | 1.16 |
| LWP 760 + LWP 320 + 0.01 mg LWP 760 Signal Peptide | 100 | 1.56 | 6,533,600 | 4,201,025 | 514.8 | 5.2 |
| LWP 760 + LWP 320 + 0.01 mg LWP 760 Signal Peptide added after about 2 hours of cultivation | 100 | 1.56 | 6,553,600 | 4,201,025 | 514.8 | 5.2 |
| LWP 760 + LWP 320 + 0.01 mg LWP 760 Signal Peptide added after about 4 hours of cultivation | 100 | 2.1 | 13,107,200 | 6,241,523 | 693 | 7 |
| LWP 760 + LWP 320 + 0.01 mg LWP 760 Signal Peptide added after about 6 hours of cultivation | 100 | 1.56 | 6,553,600 | 4,201,025 | 514.8 | 5.2 |
| LWP 760 + LWP320 + 0.001 mg LWP 760 Signal Peptide | 100 | 0.32 | 1,638,840 | 5,121,375 | 105.6 | 1.06 |
| LWP 760 + LWP 320 + 0.001 mg LWP 760 Signal Peptide added after about 2 hours of cultivation | 100 | 0.32 | 1,638,840 | 5,121,375 | 105.6 | 1.06 |
| LWP 760 + LWP 320 + 0.001 mg LWP 760 Signal Peptide added after about 4 hours of cultivation | 100 | 0.32 | 1,638,840 | 5,121,375 | 105.6 | 1.06 |
| LWP 760 + LWP 320 + 0.001 mg LWP 760 Signal Peptide added after about 6 hours of cultivation | 100 | 0.32 | 1,638,840 | 5,121,375 | 105.6 | 1.06 |
| LWP 760 + LWP 320 + 0.1 mg LWP 50-52 Signal Peptide | 100 | 0.30 | 1,638,840 | 5,462,666 | 99 | 1 |
| LWP 760 + LWP320 + 0.1 mg LWP PVD 32 Signal Peptide | 100 | 0.30 | 1,638,840 | 5,462,666 | 99 | 1 |

As seen in Table 6 above, cultivation of inducer strain LWP 760 with inducer strain 320 and approximately 0.01 mg of signal peptide from LWP 760 in 4 hours of cultivation increases the yield of bacteriocin 760 up to approximately 693 mg from one liter of culture fluid. The introduction of signal peptides from PVD 32 and LWP 50-52 did not increase the yield of bacteriocin production of bacteriocin 760 versus control.

To assess the effect of the signal peptide on bacteriocin production under scale-up conditions, LWP 760 and LWP 320 were grown in a V-6 liter bioreactor with about 6 liters of 10% *Brucella* broth. The ratio of concentrations of cultures and the signal peptide was maintained as for the condition that produced 510 mg/liter of bacteriocin 760 in the above table 7. Bacteriocin 760 was isolated approximately 8,10,12 and 14 hours after cultivation. Maximum bacteriocin production occurred after 12 hours of cultivation (Table 7 below).

TABLE 7

Cultivation of producer strain LWP 760 and inducer strain LWP 320 in the presence of LWP Signal Peptide under scaled-up conditions.

| Experimental Conditions | Fraction Volume ml | Protein Concentration mg/ml | Activity AU/ml | Specific Activity AU/mg | Protein produced per one liter of medium mg | Increase in the amount of protein produced vs. in control |
|---|---|---|---|---|---|---|
| Control | 900 | 0.8 | 3,276,800 | 4,096,000 | 120 | 1 |
| 0.22 mg Signal Peptide 760 | 900 | 3.4 | 13,107,200 | 3,855,058 | 510 | 4.25 |

Control: V-61 bioreactor, 10% Brucella Broth, LWP 760, LWP 320, at pH 6.9, 37° C., 150 r.p.m., 12 hours cultivation.
Signal Peptide: V-61 reactor, 10% Brucella Broth, LWP 760, LWP 320, LWP 760 Signal peptide-0.22 mg added after two hours of cultivation, pH 6.9, 37° C., 150 r.p.m., 12 hours cultivation.

EXAMPLE 5

Amino acid sequences for the signal peptides were determined by Edman degradation using a 491 cLC Automatic Sequencer (Applied Biosystems, La Jolla, Calif.) per manufacturer's instructions. Determination of molecular mass of each signal peptide was performed by matrix-assisted laser desorption and ionization-time of flight mass spectrometry (MALDI-TOFMS) with an electrospray-ionizing mass spectrometer (API IIITAGA 6000E, CJEX, Mumbai, India) as per manufacturers instructions. Results are shown in Table 8 below.

TABLE 8

Amino acid sequences for bacteriocins OR-7, LWP 50-52, and LWP 760 and their corresponding signal peptides.

| Sample | Amino Acid Sequence | Molecular Mass (Da)[a] |
|---|---|---|
| Bacteriocin OR-7 | KTYYGTNGVHCTKNSLWGKVRLKNMKYDQNTTYMGRLQDILLGWATGAFGKTH SEQ ID NO 2 | 5,123 |
| PVD 32 Signal Peptide | MVTKSLVLAWVVALLACGM*VKGLT* SEQ ID NO 3 | 2,347 |
| Bacteriocin 50-52 | TTKNYGNGVCNSVNWCQCGNVWASCNLATGCAAWLCKLA SEQ ID NO 4 | 3,932 |
| LWP50-52 Signal Peptide | TNVTKSWWVLAGCNQVVASNCNCGNV*KGLT* SEQ ID NO 5 | 3,065 |
| Bacteriocin 760 | NRWYCNSAAGGVGGAAVCGLAGYVGEAKENIAGEVRKGWGMAGGFTHNKACKSFPGSGWASG SEQ ID NO 6 | 5,362 |
| LWP 760 Signal Peptide | WNKYKTNWVLSVCNTGCACAAV*KGLT* SEQ ID NO 7 | 2,095 |

The foregoing detailed description is for the purpose of illustration. Such detail is solely for that purpose and those skilled in the art can make variations without departing from the spirit and scope of the invention.

We claim:

1. An isolated peptide having the carboxy terminal amino acid sequence of SEQ ID NO: 1.

2. An isolated peptide having the amino acid sequence of SEQ ID NO: 3.

3. An isolated peptide having the amino acid sequence of SEQ ID NO: 5.

4. An isolated peptide having the amino acid sequence of SEQ ID NO: 7.

* * * * *

SEQUENCE LISTING

```
<160> NUMBER OF SEQ ID NOS: 7

<210> SEQ ID NO 1
<211> LENGTH: 5
<212> TYPE: PRT
<213> ORGANISM: Bacteria

<400> SEQUENCE: 1

Val Lys Gly Leu Thr
1               5

<210> SEQ ID NO 2
<211> LENGTH: 53
<212> TYPE: PRT
<213> ORGANISM: Lactobacillus salivarius

<400> SEQUENCE: 2

Lys Thr Tyr Tyr Gly Thr Asn Gly Val His Cys Thr Lys Asn Ser Leu
1               5                   10                  15

Trp Gly Lys Val Arg Leu Lys Asn Met Lys Tyr Asp Gln Asn Thr Thr
                20                  25                  30

Tyr Met Gly Arg Leu Gln Asp Ile Leu Leu Gly Trp Ala Thr Gly Ala
            35                  40                  45

Phe Gly Lys Thr His
    50

<210> SEQ ID NO 3
<211> LENGTH: 24
<212> TYPE: PRT
<213> ORGANISM: Lactobacillus salivarius

<400> SEQUENCE: 3

Met Val Thr Lys Ser Leu Val Leu Ala Trp Val Val Ala Leu Leu Ala
1               5                   10                  15

Cys Gly Met Val Lys Gly Leu Thr
            20

<210> SEQ ID NO 4
<211> LENGTH: 39
<212> TYPE: PRT
<213> ORGANISM: Enterococcus faecium

<400> SEQUENCE: 4

Thr Thr Lys Asn Tyr Gly Asn Gly Val Cys Asn Ser Val Asn Trp Cys
1               5                   10                  15

Gln Cys Gly Asn Val Trp Ala Ser Cys Asn Leu Ala Thr Gly Cys Ala
            20                  25                  30

Ala Trp Leu Cys Lys Leu Ala
            35

<210> SEQ ID NO 5
<211> LENGTH: 30
<212> TYPE: PRT
<213> ORGANISM: Enterococcus faecium

<400> SEQUENCE: 5

Thr Asn Val Thr Lys Ser Trp Trp Val Leu Ala Gly Cys Asn Gln Val
```

-continued

```
           1               5              10              15
Val Ala Ser Asn Cys Asn Cys Gly Asn Val Lys Gly Leu Thr
                    20              25              30
```

<210> SEQ ID NO 6
<211> LENGTH: 62
<212> TYPE: PRT
<213> ORGANISM: Streptococcus cricetus

<400> SEQUENCE: 6

```
Asn Arg Trp Tyr Cys Asn Ser Ala Ala Gly Gly Val Gly Gly Ala Ala
1               5                   10                  15
Val Cys Gly Leu Ala Gly Tyr Val Gly Glu Ala Lys Glu Asn Ile Ala
                20                  25                  30
Gly Glu Val Arg Lys Gly Trp Gly Met Ala Gly Gly Phe Thr His Asn
                35                  40                  45
Lys Ala Cys Lys Ser Phe Pro Gly Ser Gly Trp Ala Ser Gly
           50              55                  60
```

<210> SEQ ID NO 7
<211> LENGTH: 26
<212> TYPE: PRT
<213> ORGANISM: Streptococcus cricetus

<400> SEQUENCE: 7

```
Trp Asn Lys Tyr Lys Thr Asn Trp Val Leu Ser Val Cys Asn Thr Gly
1               5                   10                  15
Cys Ala Cys Ala Ala Val Lys Gly Leu Thr
                20                  25
```